(12) United States Patent
Serata et al.

(10) Patent No.: US 7,794,763 B2
(45) Date of Patent: Sep. 14, 2010

(54) **BACTERIUM OF THE GENUS *BIFIDOBACTERIUM* AND FERMENTED FOODS USING THE SAME**

(75) Inventors: Masaki Serata, Tokyo (JP); Hirokazu Tsuji, Tokyo (JP); Koichiro Sonoike, Tokyo (JP)

(73) Assignee: Kabushiki Kaisha Yakult Honsha, Tokyo (JP)

( * ) Notice: Subject to any disclaimer, the term of this patent is extended or adjusted under 35 U.S.C. 154(b) by 1257 days.

(21) Appl. No.: 10/493,068

(22) PCT Filed: Nov. 1, 2002

(86) PCT No.: PCT/JP02/11440

§ 371 (c)(1),
(2), (4) Date: Oct. 1, 2004

(87) PCT Pub. No.: WO03/040350

PCT Pub. Date: May 15, 2003

(65) Prior Publication Data

US 2005/0031735 A1    Feb. 10, 2005

(30) Foreign Application Priority Data

Nov. 5, 2001   (JP) .............................. 2001-339012

(51) Int. Cl.
*A23C 9/12*    (2006.01)
(52) U.S. Cl. ................. 426/42; 426/34; 426/43; 424/93.4; 435/243; 435/244; 435/252.1
(58) Field of Classification Search ................ 424/93.4; 426/34, 42, 43; 435/243, 244, 252.1
See application file for complete search history.

(56) References Cited

U.S. PATENT DOCUMENTS

| | | | |
|---|---|---|---|
| 4,091,117 A | 5/1978 | Mutai et al. | |
| 4,187,321 A * | 2/1980 | Mutai et al. | .......... 426/43 |
| 4,601,985 A | 7/1986 | Okonogi et al. | |
| 4,870,020 A | 9/1989 | Sozzi | |
| 5,695,796 A * | 12/1997 | Yamamoto et al. | .......... 426/43 |
| 5,711,977 A * | 1/1998 | Yang et al. | .......... 426/61 |
| 6,306,638 B1 | 10/2001 | Yang et al. | |
| 6,548,057 B1 * | 4/2003 | Shimakawa et al. | ........ 424/93.4 |

FOREIGN PATENT DOCUMENTS

| | | |
|---|---|---|
| EP | 111392 | 6/1984 |
| EP | 0 974 268 A1 | 1/2000 |
| EP | 1010 753 A1 * | 6/2000 |
| JP | 57-99190 | 6/1982 |
| JP | 4-320642 | 11/1992 |

OTHER PUBLICATIONS

Holland K.T. et al. 1987. Anaerobic Bacteria. Chapman & Hall, New York.*
Frank A. M. Klaver, et al. "Growth and survival of bifidobacteria in milk", Netherlands Milk Dairy Journal, XP 000422987, vol. 47, No. 3/4, 1993, pp. 151-164.

* cited by examiner

*Primary Examiner*—Keith D Hendricks
*Assistant Examiner*—Hamid R Badr
(74) *Attorney, Agent, or Firm*—Oblon, Spivak, McClelland, Maier & Neustadt, L.L.P.

(57) ABSTRACT

The present invention provides a bacterium belonging to the genus *Bifidobacterium*, which can exhibit a high viability in the storage under agitation and can produce a fermented food containing a large number of viable bacterial count. The present invention further provides a fermented food, which contains the bacterium belonging to the genus *Bifidobacterium* and exhibits various physiological effects such as inhibitory action against harmful intestinal bacteria and intestinal function controlling effects. The present invention further provides a bacterium belonging to the genus *Bifidobacterium* having a rate of viability of 30% or more, when the bacterium is stored in the aerobic condition under agitation at 10° C. for 14 days after culturing in a medium containing milk as a main ingredient until obtaining a viable count of $1 \times 10^8$ cfu/ml or more, and fermented food using the same.

8 Claims, 1 Drawing Sheet

BACTERIUM OF THE GENUS *BIFIDOBACTERIUM* AND FERMENTED FOODS USING THE SAME

TECHNICAL FIELD

The present invention relates to bacteria belonging to the genus *Bifidobacterium* having a high viability even after storing under agitation, and fermented foods containing the same.

BACKGROUND ART

Bacteria belonging to the genus *Bifidobacterium* are obligate anaerobes and are weak in an aerobic condition. In fermentation products, it is difficult to handle in view of proliferation during the production and viability under storing. In order to obtain physiological effects (intestinal function controlling effect or the like) of the bacteria belonging to the genus *Bifidobacterium*, they must reach the intestine in a viable form as much as possible. It is thought to be an important factor in the production of the fermented foods of this type to increase in the viability of bacteria in the fermented foods and an arriving rate of bacteria to the intestine after meal.

As a result of improvement in bacterial strains by various methods, strains improved in proliferation and viability have recently been prepared. In addition, an improvement in viability is performed also in fermented foods by an improvement of production process and addition of various agents for improving the viability, such as N-acetyl glucosamine, pantothenic acid, pantethine, pantetheine, peptides and lactulose.

However, in the production site of the fermented foods, it is difficult to pack all fermented products of *Bifidobacterium* bacteria on the same day from the viewpoint of production cost and working ability, and at present, semimanufactured products products admixed with other additives or the like are stored in the aerobic storage tank for several days. In order to stably supply a product with a superior viability satisfying a quality standard for maintaining high viable count even under such aerobic circumstance, further improvement in the viability is required.

Under such circumstance, viable bacteria living in severe conditions such as aerobic condition or addition of acid did not always exhibit increased viability. As a result, it was extremely difficult to obtain a bacterial strain having more superior viability as compared with known bacteria. Further, even by the improvement of the production process and the addition of various viability improving agents, it was difficult to maintain the viability of bacteria in the fermented foods which were aerobically stored in the production site, at a sufficiently high level even after shipment of the products.

Consequently, an object of the present invention is to provide a bacterium belonging to the genus *Bifidobacterium* having a high viable count and good viability, even after storing for desired term until packing into a vessel and shipping to the market after fermentation of the bacterium, and fermented foods produced by using the same.

DISCLOSURE OF THE INVENTION

Taking such actual circumstances into consideration, the present inventors studied extensively and paid attention on the fact that in the storage of fermented milk before shipment, an agitation treatment was commonly given in a tank in order to maintain uniformity of the fermented foods. During the production of fermented foods, it was thought that *Bifidobacterium* bacteria were forced to be exposed to severe environment for the bacteria. The present inventors found that the viability of bacterium in the fermented product was significantly improved, when the bacterium belonging to the genus *Bifidobacterium* having a nature exhibiting a high viable count after aerobic storage with agitation was selected, and the fermented product, produced by fermenting using the bacterium, was stored with agitation. The present inventors also found that viability of bacteria under the storing condition was significantly improved, when fermented foods were produced by using said fermented product, and thereby completed the present invention.

Namely, an object of the present invention is to provide a bacterium belonging to the genus *Bifidobacterium* having a rate of viability of 30% or more, when the bacterium is stored in the aerobic condition under agitation at 10° C. for 14 days after culturing in a medium containing milk as a main ingredient until obtaining a viable count of $1 \times 10^8$ cfu/ml or more.

Another object of the present invention is to provide a fermented food containing a fermented product fermented with the bacterium belonging to the genus *Bifidobacterium*.

Further object of the present invention is to provide a fermented food containing bacteria belonging to the genus *Bifidobacterium* in a fermented food containing a fermented product fermented with one or more bacteria belonging to the genus *Bifidobacterium*, wherein a viable count of the bacteria belonging to the genus *Bifidobacterium* in said food immediately after production is $1 \times 10^8$ cfu/ml or more, and a rate of viability of any one of the bacteria belonging to said genus *Bifidobacterium* is 30% or more, when the food is stored in the aerobic condition under agitation at 10° C. for 14 days.

BEST MODE FOR CARRYING OUT THE INVENTION

Figure 1:
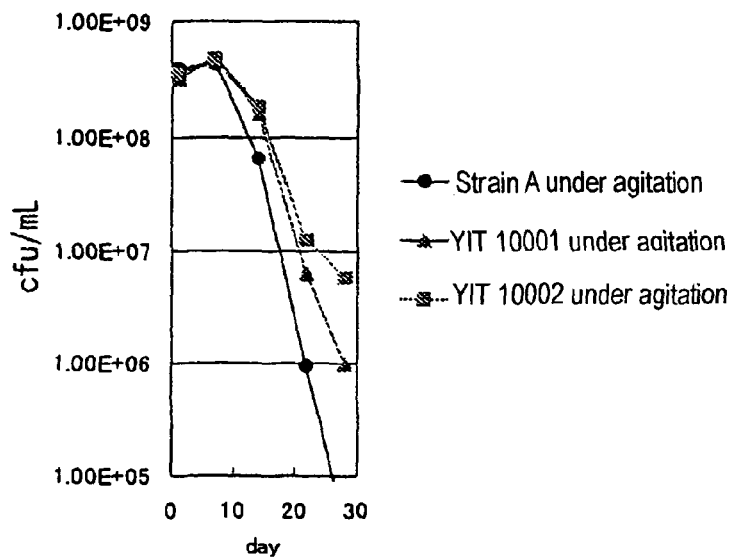
FIG. 1 shows viable counts of various strains, when fermented milk products containing each strain are stored under agitation at 10° C. in Example 2.

Bacteria belonging to the genus *Bifidobacterium* of the present invention are the bacteria having a rate of viability of 30% or more, when the bacteria are stored in the aerobic condition under agitation at 10° C. for 14 days after culturing in a medium containing milk as a main ingredient until obtaining a viable count of $1 \times 10^8$ cfu/ml or more. The medium containing milk as a main ingredient herein is the medium containing milk as a main nutrient source and capable of growth of the bacteria belonging to the genus *Bifidobacterium*. Examples of the milk include cow's milk (whole milk) and skim milk as a processed product thereof.

Culture condition for culturing the bacteria belonging to the genus *Bifidobacterium* in the medium is not particularly limited, and may be suitably set depending on the growth condition of the bacteria belonging to the genus *Bifidobacterium* used. Culture is performed generally at 30 to 40° C., preferably at 33 to 37° C., preferably under anaerobic condition. Among the bacteria belonging to the genus *Bifidobacterium*, some strains are difficult to grow by a nutrient source of milk alone. In such case, essential nutrient source and growth promoting substance for *Bifidobacterium* bacteria such as various sugars, yeast extract, peptide and the like may be added. Further, it can also be simultaneously cultured with lactic acid bacteria such as *Lactococcus lactis* which can promote growth of *Bifidobacterium* bacteria by cocultivating therewith.

Among media used for culturing *Bifidobacterium* bacteria, a medium which can be generally used include a liquid medium containing 20% by weight (hereinafter simply designated as %) of skim milk and 0.03% of Meast. Almost all *Bifidobacterium* bacteria can be grown in said medium, and the bacteria of the present invention are able to exhibit a viability of 30% or more in the above storage condition under agitation after culturing up to a viable count of $1 \times 10^9$ cfu/ml or more.

As the *Bifidobacterium* bacteria of the present invention, the strain exhibiting a rate of viability of 30% or more after culturing up to a viable count of $1 \times 10^9$ cfu/ml or more in said medium is particularly preferable.

Generally, in the production of food and drink products containing *Bifidobacterium* bacteria such as fermented milk, since it is required to obtain a large viable count with small amount, the product is designed for maintaining a viable count of $1 \times 10^7$ cfu/ml or more in the product after storage. The strain, as like the present invention, having a viable count of $1 \times 10^8$ cfu/ml or more and a high rate of viability after storage with agitation has high tolerability (rate of viability) for agitation in the food and drink product with a high viable count, and at the same time, when the product is stored by standing after storage with agitation, i.e. after the product is manufactured into a commercial form, the rate of viability in the storage state is significantly high. Especially, strains having a high rate of viability after culturing up to a viable count of $1 \times 10^9$ cfu/ml or more are superior in the above effect.

Further, in the present invention, the storage with agitation means that cultured products, in which *Bifidobacterium* bacteria are cultured in the medium containing milk as a main ingredient, or fermented foods appropriately prepared by mixing with syrup or the like are stored under the condition with continued agitation by using stirring bar or mixing propeller in the aerobic condition.

Confirmation of the rate of viability of *Bifidobacterium* bacteria is performed by using a method, in which, specifically, 300 ml of cultured product or fermented food is charged into 300 ml flask with a stirring bar, cotton plugged, and stored under stirring at about 120 rpm by using magnetic stirrer in an incubator at 10° C.

Rate of viability indicates an extent to which the viable bacterial cells exist after storage, and viable count can be measured by the conventional method. For example, viable count can be obtained by spreading a properly diluted fermented product (food) containing viable cells on TYL agar plate medium, culturing anaerobically at 37° C. for 72 hours, and counting the number of colonies on the medium.

In the present invention, "rate of viability" means a rate of the viable count after storage under stirring (at 10° C. for 14 days) to the viable count of the cultured liquid, which is cultured up to a viable count of $1 \times 10^8$ cfu/ml or more in the medium containing milk as a main ingredient, or the viable count before storage in the fermented food immediately after production.

The *Bifidobacterium* bacteria having the rate of viability of 30% or more in such storage under agitation can not only give a high rate of viability, even after the storage under agitation in the tank, when a fermented food is produced by using said strain, but also maintain the high viability even after manufacturing and storing a commercial product. Consequently, *Bifidobacterium* bacteria of the present invention are quite useful.

In the present invention, species of the bacterium belonging to the genus *Bifidobacterium* is not particularly limited. For example, *Bifidobacterium breve*, *Bifidobacterium bifidum*, *Bifidobacterium longum*, *Bifidobacterium infantis*, *Bifidobacterium catenulatum*, *Bifidobacterium animalis*, *Bifidobacterium pseudocatenulatum* and *Bifidobacterium adolescentis* can be suitably used. Among them, *Bifidobacterium breve*, *Bifidobacterium bifidum* and *Bifidobacterium longum* are preferable, since viability improving effects thereof after production of fermented foods are high, and safeties thereof are sufficiently confirmed, and *Bifidobacterium breve* is particularly preferable.

Such strains having a high rate of viability after storing under agitation can be obtained, for example, by culturing parent strain of *Bifidobacterium* bacteria, storing the thus obtained fermented product with agitation for about 2 weeks, and selecting a highly resistant strain from viable cells.

The present inventors have selected two strains which were recognized to have a high rate of viability after storing under agitation. Strains *Bifidobacterium breve* YIT 10001 (FERM BP-8205) and *Bifidobacterium breve* YIT 10002 (FERMBP-8206) were deposited in International Patent Organism Depositary, National Institute of Advanced Industrial Science and Technology (Chuo No. 6), 1-1, Higashi-1-chome, Tsukuba, Ibaraki, 305-8566 Japan) on Aug. 14, 2001.

*Bifidobacterium breve* YIT 10001 and *Bifidobacterium breve* YIT 10002 have following taxonomical properties.

TABLE 1

|  | YIT 10001 | YIT 10002 |
| --- | --- | --- |
| Gram stain | positive | positive |
| Morphology | Rods of various shapes | Rods of various shapes |
| Catalase | – | – |
| Gas production from glucose | – | – |
| Growth at |  |  |
| 20° C. | – | – |
| 30° C. | ± | ± |
| 37° C. | + | + |
| 40° C. | + | + |
| 45° C. | – | – |
| in 0.2% bile | ± | ± |
| Hydrolysis of arginine | – | – |
| Benzidine test | – | – |
| Nitrate reduction | – | – |

TABLE 2

|  | YIT 10001 | YIT 10002 |
| --- | --- | --- |
| Glycerol | – | – |
| Erythritol | – | – |
| D-Arabinose | ± | ± |
| L-Arabinose | – | – |
| Ribose | + | + |
| D-Xylose | – | – |
| L-Xylose | – | – |
| Adonitol | – | – |
| β-Methyl-xyloside | – | – |
| Galactose | + | + |
| D-Glucose | + | + |
| D-Fructose | + | + |
| D-Mannose | + | + |
| L-Sorbose | – | – |
| Rhamnose | – | – |
| Dulcitol | – | – |
| Inositol | – | – |
| Mannitol | – | – |
| Sorbitol | – | – |
| α-Methyl-D-mannoside | – | – |

TABLE 2-continued

|  | YIT 10001 | YIT 10002 |
| --- | --- | --- |
| α-Methyl-D-glucoside | + | + |
| N-Acetyl glucosamine | − | − |
| Amygdaline | − | + |
| Arbutine | + | + |
| Esculin | + | + |
| Salicin | + | + |
| Cellobiose | + | + |
| Maltose | + | + |
| Lactose | + | + |
| Melibiose | + | + |
| Saccharose | + | + |
| Treharose | − | − |
| Inulin | − | − |
| Melezitose | + | + |
| D-Raffinose | + | + |
| Amidon | − | ± |
| Glycogen | − | − |
| Xylitol | − | − |
| β-Gentiobiose | − | + |
| D-Turanose | + | + |
| D-Lyxose | − | − |
| D-Tagatose | − | − |
| D-Fucose | − | − |
| L-Fucose | W | W |
| D-Arabitol | − | − |
| L-Arabitol | − | − |
| Gluconate | − | − |
| 2-ceto-gluconate | − | − |
| 5-ceto-gluconate | − | − |

+: positive,
W: weakly positive,
±: false positive,
−: negative

The strain having a high rate of viability after storage under agitation can also be obtained by treating with ultraviolet ray or mutagenic agents such as nitrosoguanidine (NTG) and ethyl methansulfonate (EMS).

The fermented food of the present invention contains at least one fermented product which is fermented by the above exemplified bacteria belonging to the genus *Bifidobacterium*. When the fermented food immediately after production (which contains *Bifidobacterium* bacteria having a viable count of $1\times10^8$ cfu/ml or more) is stored under agitation at 10° C. for 14 days in the aerobic condition, a rate of viability of the *Bifidobacterium* bacteria is 30% or more. Examples of the fermented food include fermented milk, fermented soybean milk, fermented fruit juice and fermented vegetable milk, and the fermented milk and fermented soybean milk are particularly preferable due to significantly improved viabilities thereof after storage of the product.

The fermented food preferably contains the *Bifidobacterium* bacteria having a viable count of $1\times10^9$ cfu/ml or more in the fermented product after cultivation, and contains $1\times10^8$ cfu/ml or more immediately after manufacturing the product by adding other components. When the bacteria are grown to such extent, a particularly superior improved effect in viability can be obtained as compared with use of other strains (e.g. parent strain).

In the production of the fermented food, microorganisms other than the *Bifidobacterium* bacteria of the present invention may be used in combination. Examples of such microorganisms include: bacteria belonging to the genus *Lactobacillus* such as *Lactobacillus acidophilus, Lactobacillus gasseri, Lactobacillus plantarum, Lactobacillus buchneri, Lactobacillus casei, Lactobacillus johnsonii, Lactobacillus gallinarum, Lactobacillus amylovorus, Lactobacillus brevis, Lactobacillus rhamnosus, Lactobacillus kefir, Lactobacillus paracasei, Lactobacillus crispatus, Lactobacillus delbrueckii* subsp. *delbrueckii, Lactobacillus delbrueckii* subsp. *bulgaricul, Lactobacillus helveticus, Lactobacillus zeae* and *Lactobacillus salivalius*; bacteria belonging to the genus *Streptococcus* such as *Streptococcus thermophilus*; bacteria belonging to genus *Lactococcus* such as *Lactococcus lactis* subsp. *cremoris* and *Lactococcus lactis* subsp. *lactis*; bacteria belonging to the genus *Bacillus* such as *Bacillus subtilis*; and yeast belonging to the genus *Saccharomyces, Torulaspora* and *Candida* such as *Saccharomyces cerevisiae, Torulaspora delbrueckii* and *Candida kefyr*.

Among these, bacteria belonging to the genus *Lactobacillus*, the genus *Streptococcus* and the genus *Lactococcus* are preferable, because a fermented milk product, produced by combining one or more bacteria selected therefrom, has a superior acceptability and is easy to drink continually. These bacteria are also preferable due to improved effect for viability.

The fermented product of the present invention can be produced by the conventional methods. For example, in order to produce a fermented milk, firstly a bacterium belonging to the genus *Bifidobacterium* is inoculated alone or in combination with other microorganism in a sterilized milk medium, and cultured to obtain a fermented milk base after homogenization. A separately prepared syrup solution is added thereto and mixed, and homogenized by using a homogenizer, and then flavor is added to prepare a final product.

The thus obtained fermented milk of the present invention can be processed to any type of product such as plane type, soft type, fruit flavor type, solid type and liquid type.

Food materials used in the conventional fermented food such as various sugars, emulsifier, thickener, sweetener, acidifier and fruit juice can optionally be admixed. Specific examples thereof include: sugars such as sucrose, isomerized sugar, glucose, fructose, palatinose, trehalose, lactose and xylose; sugar alcohol such as sorbitol, xylitol, erythritol, lactitol, palatinit, reduced glutinous starch syrup and reduced glutinous maltose syrup; emulsifier such as sucrose esters of fatty acid, glycerin esters of fatty acid and lecithin; thickener (stabilizer) such as carrageenan, xanthan gum, guar gum, pectin and locust bean gum; acidifier such as citric acid, lactic acid and malic acid; and fruit juice such as lemon juice, orange juice and berry juice. Vitamins such as vitamin A, vitamin B, vitamin C, vitamin D and vitamin E and minerals such as calcium, iron, manganese and zinc can also be added.

EXAMPLES

The present invention will be explained in more detail by Examples, but the present invention is not limited to these Examples.

Example 1

A parent strain, a strain of *Bifidobacterium breve* (YIT 4065: FERM BP-6223, deposited in International Patent Organism Depositary, National Institute of Advanced Industrial Science and Technology (Chuo No. 6, 1-1, Higashi-1-chome, Tsukuba, Ibaraki, 305-8566 Japan) on Feb. 2, 1996) (cephalothin-streptomycin resistant strain) and *Lactococcus lactis* were inoculated into a medium containing 20% skim milk, and mix-cultured at 37° C. for 24 hours to prepare a bacterial solution. To this bacterial solution, a bacterial solution obtained by culturing *Streptococcus thermophilus* using 20% skim milk at 37° C. for 20 hours was added (mixing ratio=1:2). A syrup solution containing reduced glutinous maltose syrup was added to a final concentration of 5% to prepare a fermented milk product. The fermented milk product was poured into a glass bottle and was agitated using stirrer under aerobic environment with cotton plugged during storage period. Under this condition, the bottle was stored at 10° C. for 2 weeks. Viable bacteria were smeared on the medium, and 2,000 strains of single colony were isolated.

The fermented milk product was prepared with the isolated strains and the parent strain of the strain of *Bifidobacterium* A by the same way as described above. Into a 300 ml flask with stirrer, 300 ml of the mixture was poured, cotton plugged and stored with agitation at 120 rpm using stirrer. Viabilities of bacteria during the storage were compared, and two strains which showed superior viabilities than the strain A were obtained. Viability after 2 weeks of storage under agitation is shown in Table 3. Two strains (YIT 10001 and YIT 10002) exhibited 30% or more of viabilities after 2 weeks of storage under agitation. Viable counts were performed using the TYL medium having a composition shown in Table 4.

TABLE 3

| Strain | Rate of viability (%) | Initial viable count (cfu/ml) |
|---|---|---|
| Strain A | 11 | $5.6 \times 10^8$ |
| YIT 10001 | 31 | $5.22 \times 10^8$ |
| YIT 10002 | 33 | $5.54 \times 10^8$ |

TABLE 4

| Composition of TYL medium | |
|---|---|
| Trypticase peptone (BBL) | 1.0 (%) |
| Yeast extract (Difco) | 0.5 |
| Lab lemco powder (Oxoid) | 0.3 |
| Potassium dihydrogen phosphate | 0.3 |
| Dipotassium hydrogen phosphate | 0.48 |
| Ammonium sulfate | 0.3 |
| Magnesium sulfate | 0.02 |
| L-cysteine | 0.05 |
| Lactose | 1.0 |
| Agar | 1.2 |

Example 2

Viability Test

Bifidobacterium breve YIT 10001, YIT 10002 and strain A as the bacteria belonging to the genus *Bifidobacterium* were used to prepare fermented milk products.

Namely, 2 lit. of 20% milk medium was charged into a 2.5 L jar-fermenter, strains of the bacteria belonging to the genus *Bifidobacterium* hereinabove and *Lactococcus lactis* YIT 2027 were inoculated as seed starters in 2% and 0.01%, respectively, and cultured at 37° C. for 24 hours to prepare a bacterial solution by homogenizing at 15 Mpa. *Streptococcus thermophilus* was cultured in 20% skim milk at 37° C. for 20 hours to prepare a bacterial solution by homogenizing at 15 Mpa. These bacterial solutions were mixed at a ratio of 1:2, and a syrup solution containing reduced glutinous maltose syrup was added to the final concentration of 5% to prepare a fermented milk product (viable counts were: strain A $5.65 \times 10^8$ cfu/ml, YIT 10001 $5.34 \times 10^8$ cfu/ml, and YIT 10002 $5.45 \times 10^8$ cfu/ml).

Figure 2:
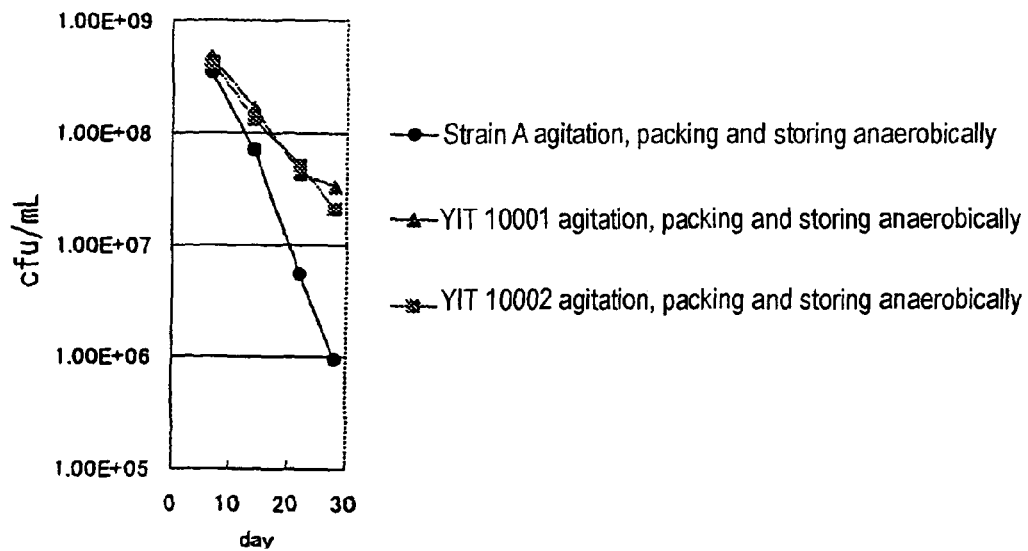
FIG. 2 shows viable counts of various strains, when fermented milk products containing each strain are stored under agitation at 10° C. for 1 week, packed and stored anaerobically at standing.

Viable counts of these samples were measured by the same way as in Example 1 after storage under agitation at 10° C., or after agitating for 1 week and packing into a test tube, and then anaerobically stored by replacing the air with nitrogen gas. Results are shown in FIG. 1 and FIG. 2.

Viabilities of YIT 10001 and YIT 10002 stored for 14 days exceeded 30% and were improved as compared with the strain A. Viabilities of both strains after stored under agitation and maintained by standing storage were also improved significantly as compared with the strain A.

Example 3

In a 2.5 lit. jar-fermenter, 2 lit. of 24% milk medium was charged. Seed starters of *Bifidobacterium breve* YIT 10001 and *Lactococcus lactis* YIT 2027 were inoculated, in 2% and 0.01%, respectively, and cultured at 37° C. for 24 hours to prepare a bacterial solution by homogenizing at 15 Mpa. Seed starters of *Lactobacillus casei* and *Lactobacillus acidophilus* were inoculated each in 0.5% in 20% skim milk, cultured at 37° C. for 24 hours to prepare a bacterial solution by homogenizing at 15 Mpa. These bacterial solutions were mixed at a ratio of 2:3, and a syrup solution containing palatinose was added to a final concentration of 10% to prepare a fermented milk product (Initial viable count of YIT 10001: $5.76 \times 10^8$ cfu/ml).

In the fermented milk product, YIT 10001 exhibited a rate of viability of 30% or more after the storage at 10° C. for 2 weeks under agitation in the same way as in Example 1. Taste was also good.

INDUSTRIAL APPLICABILITY

Bacteria belonging to the genus *Bifidobacterium* of the present invention exhibits a high rate of viability even after storage under agitation, and a fermented food containing a large amount of viable microorganisms can be produced. Consequently, the fermented food of the present invention contains a high viable count, and exhibits a high physiological effect such as suppressive action against harmful intestinal bacteria and intestinal function controlling effects possessed by the bacteria belonging to the genus *Bifidobacterium*.

What is claimed is:

1. A bacterium belonging to the genus *Bifidobacterium* having a rate of viability of 30% or more, when the bacterium is stored in the aerobic condition under agitation at 10° C. for 14 days after culturing in a medium containing milk as a main ingredient until obtaining a viable count of $1 \times 10^8$ cfu/ml or more, wherein the bacterium is *Bifidobacterium breve* YIT 10001.

2. A fermented food comprising a fermented product fermented by a bacterium belonging to the genus *Bifidobacterium* according to claim 1.

3. The fermented food according to claim 2 comprising fermented milk.

4. The fermented food according to claim 2, further containing a sweetener.

5. A fermented food comprising bacteria belonging to the genus *Bifidobacterium* in a fermented food comprising a fermented product fermented with one or more bacteria belonging to the genus *Bifidobacterium* according to claim 1, wherein a viable count of the bacteria belonging to the genus *Bifidobacterium* in said food immediately after production is $1 \times 10^8$ cfu/ml or more, and a rate of viability of any one of the bacteria belonging to said genus *Bifidobacterium* is 30% or more, when the food is stored in the aerobic condition under agitation at 10° C. for 14 days, and wherein the bacteria belonging to the genus *Bifidobacterium* are *Bifidobacterium breve* YIT 10001.

6. A method for producing a bacterium belonging to the genus *Bifidobacterium* having a rate of viability of 30% or more, when the bacterium is stored in aerobic conditions, the method comprising:

a) inoculating *Bifidobacterium* and *Lactococcus lactis* into a medium comprising 20% by weight of skim milk, b) culturing the mixture of a) at 30 to 40° C. for 24 hours under anaerobic conditions, c) adding to the culture of b) a bacterial solution, wherein the bacterial solution is a solution of (a) *Streptococcus thermophilus* or (b) *Lactobacillus casei* and *Lactobacillus acidophilus*, d) adding a syrup solution comprising a reduced glutinous maltose syrup to a final concentration of 5% to prepare a fermented milk product, e) storing the fermented milk product under agitation and aerobic conditions at 10° C. for 14 days, and f) smearing a viable bacteria on a medium and isolating the *Bifidobacterium* having a rate of viability of 30% or more, wherein the bacterium belonging to the genus *Bifidobacterium* is *Bifidobacterium breve* YIT 10001.

7. The method for producing a bacterium belonging to the genus *Bifidobacterium* of claim 6, wherein the bacterial solution of c) is obtained by culturing *Streptococcus thermophilus* using 20% skim milk at 37° C. for 20 hours, and wherein a mixing ratio of the culture and the bacterial solution is 1:2.

8. The method for producing a bacterium belonging to the genus *Bifidobacterium* of claim 6, wherein the bacterial solution of c) is obtained by culturing *Lactobacillus casei* and *Lactobacillus acidophilus* using 20% skim milk at 37° C. for 20 hours, and wherein a mixing ratio of the culture and the bacterial solution is 2:3.

* * * * *